United States Patent [19]

Smith, III

[11] Patent Number: 4,900,685
[45] Date of Patent: Feb. 13, 1990

[54] ANALYTE DETECTION IN PARTICULATE-CONTAINING SAMPLES

[75] Inventor: Nathan L. Smith, III, North Andover, Mass.

[73] Assignee: Cytosignet, Inc., North Andover, Mass.

[21] Appl. No.: 8,571

[22] Filed: Jan. 29, 1987

[51] Int. Cl.$^4$ ............... G01N 33/554; G01N 33/555
[52] U.S. Cl. ................... 436/519; 436/520; 436/523; 436/531
[58] Field of Search ............... 436/520, 523, 519, 531

[56] References Cited

U.S. PATENT DOCUMENTS

| | | | |
|---|---|---|---|
| 3,562,384 | 2/1971 | Arquilla | 436/519 |
| 3,882,225 | 5/1975 | Patel et al. | 436/519 |
| 4,398,894 | 8/1983 | Yamamoto | 436/524 X |
| 4,403,037 | 9/1983 | Coates | 436/520 X |
| 4,433,059 | 2/1984 | Chang et al. | |
| 4,436,827 | 3/1984 | Tamagawa | 436/534 |
| 4,547,466 | 10/1985 | Turanchik et al. | 436/534 X |
| 4,554,257 | 11/1985 | Aladjem et al. | 436/534 X |
| 4,565,789 | 1/1986 | Liotta et al. | 436/519 X |
| 4,578,360 | 3/1986 | Smith | 436/531 X |
| 4,587,222 | 5/1986 | Guffroy | 436/520 X |
| 4,594,327 | 6/1986 | Zuk | 436/520 X |
| 4,598,051 | 7/1986 | Papahadjopoulos et al. | 436/520 X |
| 4,829,011 | 5/1989 | Gibbons | 436/512 |

FOREIGN PATENT DOCUMENTS

| | | |
|---|---|---|
| 0000102 | 12/1978 | European Pat. Off. . |
| 0034050 | 8/1981 | European Pat. Off. . |
| 0143574 | 6/1985 | European Pat. Off. . |
| 1961541 | 6/1970 | Fed. Rep. of Germany . |
| 1617644 | 4/1971 | Fed. Rep. of Germany . |

OTHER PUBLICATIONS

Nichols et al., *Laboratory Manual of Clinical Immunology*, (Rose et al., ed.), 1985, pp. 49–56.
Kabat, Structural Concepts in Immunology and Immunochemistry, 1968, pp. 46–48.
B. E. Kemp et al., *Science*, 241:1352–1354, (1988).

*Primary Examiner*—Barry S. Richman
*Assistant Examiner*—Jill Johnston
*Attorney, Agent, or Firm*—Hamilton, Brook, Smith & Reynolds

[57] ABSTRACT

A method of determining the presence and quantity of an analyte of interest in a particulate-containing sample is disclosed, as is a construct for use in the method. The method is particularly useful for determining an analyte in whole blood and in fermentation suspensions. The construct is comprised of a first moiety, which is a particulate-binding moiety and a second moiety, which binds the analyte of interest.

52 Claims, 1 Drawing Sheet

ANALYTE DETECTION IN PARTICULATE-CONTAINING SAMPLES

DESCRIPTION

BACKGROUND OF THE INVENTION

Immunoassays are a type of ligand-binding assay and are widely used to determine the presence and quantities of analytes (i.e., substances or chemical constituents of a sample which are being detected). Agglutination immunoassays are a type of immunoassay in which the immunochemical reaction results in clumping of particulates such as red blood cells or polymeric latex particles. The use of immunochemical reactions as a means of causing agglutination has found application in the determination of many analytes, as described in: Nichols, W. S. and R. M. Nakamura, "Agglutination and Agglutination Inhibition Assays", *Laboratory Manual of Clinical Immunology* (Rose et al., ed.) 49–56 (1985).

For example, blood typing is performed by agglutination assays in which reagent antibody is added; red blood cells in the sample clump as a result of interaction between the added reagent antibody and antigens on the cell surfaces. Hemagglutination tests are immunoassays which use specially treated red blood cels. Such tests have been used for detecting antibodies and antigens, such as rubella antibody, rheumatoid factor, hepatitis antibody, hepatitis antigen and pregnancy hormone.

Reagents used in hemagglutination assays can be red blood cells (erythrocytes) which have antigens or antibodies bound to their surfaces. Red blood cells can be stabilized by cross linking or by treatment with tanning agents. See, for example, processes such as those taught in U.S. Pat. Nos. 4,403,037 and 4,587,222. For example, U.S. Pat. No. 4,403,037 describes preparation of antigen-coated erythrocytes with a cross-linking agent for the dual purpose of stabilizing the coated erythrocytes and reducing their hemagglutinating activity. Reduction of hemagglutinating activity is described as preventing the antigen-coated erythrocytes from undergoing spontaneous agglutination in the absence of antibody specific to red-blood-cell-bound hemagglutinating antigen. U.S. Pat. No. 4,587,222 describes a reagent containing red blood cells and soluble antibodies, as well as a process for making the reagents which involves subjecting its components to treatment with aldehydes or tanning agents.

Processes such as these can increase the useful life of the reagent red cells, but such chemical treatment also converts the flexible cell membrane to a rigid membrane and alters the surface properties of the cells. In some cases these changes adversely affect the specificity of the reagent in the assay.

For these reasons, polymeric latex particles have been used instead of red blood cells in some agglutination assays, such as in the agglutination assay for rheumatoid factor described in U.S. Pat. No. 4,547,466, which describes a method of preparing latex particles having immune complexes attached to their surfaces, and use of such particles.

However, reagent red blood cells and reagent polymeric particles both have the disadvantage of being likely to agglutinate even in the absence of the analyte being determined. In the case of reagent red blood cells, nonspecific agglutination is common and results from the presence of blood group antibodies and heterophile antibodies in the sample. In the case of polymeric particles, non-specific agglutination results from non-specific adsorption of proteins and other molecules in the sample to the particles.

Before presently-available methods based on agglutination can be carried out, it is generally necessary to remove the red blood cells from the sample. One exception to this is seen in blood-typing analyses, for which this is not necessary. Removal of red blood cells is not only an extra step in the procedure, but also one which may remove or alter the reactivity of the analyte being determined. U.S. Pat. No. 4,594,327 describes an immunochromatographic method for determination of an analyte in whole blood, in which two functions are combined in one step: separation of interfering cells (e.g., red blood cells) through binding to a binding agent and determination of the analyte.

U.S. Pat. Nos. 4,578,360 and 4,529,712 describe materials designed for use in immunoassay of antigens or antibodies; methods in which they are used are not agglutination immunoassays, but rely on other techniques of detecting analyte. In U.S. Pat. No. 4,578,360, Smith describes a mixed binding reagent (MBR) containing an antigen-binding site and a label-binding site; the reagent is described as normally consisting of two antibodies. In the method described, presence of an analyte (e.g., an antigen) is determined by mixing an analyte-containing sample with the MBR and a labelled substance and determining the quantity of labelled substance bound to the label-binding site of the MBR. In U.S. Pat. No. 4,529,712, heterobifunctional reagents are described for use in conjugating substances (e.g., antigens, antibodies) to membranes of cells or liposomes, which can then be used in hemolytic or immunocytoadherence assays.

Results of agglutination assays have generally been assessed visually, as described by Nichols and Nakamura. Nonvisual methods can also be used in some cases to detect agglutination. For example, U.S. Pat. Nos. 4,398,894; 4,436,827; and 4,554,257 describe nonvisual methods. These methods can be used for measuring hemagglutination assays.

DISCLOSURE OF THE INVENTION

The present invention relates to a method and reagent useful for ligand-binding assays, particularly immunoassays. The method of the present invention makes it possible to perform such assays on particulate-containing samples, such as whole blood. Particulates present in the samples are used as indicator particles. In samples which are suspensions of a single type of particulate, such as samples obtained from microbial fermentation or tissue culture, the single type of particulate present serves as indicator particles in the assay performed. In samples which are suspensions of two or more types of particulates (e.g., in whole blood), one type of particulate (e.g., in whole blood, red blood cells) is selected to serve as the indicator particle.

The method described has several advantages over presently-available methods. First, reagents used in the method have greater stability than those used in conventional methods. This increase in useful life occurs because, unlike reagents used in presently-available agglutination immunoassay techniques, those used in the present method contain no cells or other particulates. Second, nonspecific agglutination occurs less often than in presently-available methods because the indicator particles (which occur naturally in a nonagglutinated state) are in equilibrium with the sample and are not subject to nonspecific antibody- or adsorption-mediated agglutination. Third, because there is no chemical treatment (e.g., crosslinking, treatment with tanning agents) of the indicator particles (e.g., red blood cells), their membranes retain their flexibility, enhancing the surface contact between the particles. Thus, cell surface properties are not altered. Fourth, because the method of the present invention makes it possible to carry out ligand-binding assays on particulate-containing samples (e.g., whole blood), analytes removed by clotting or cell removing processes which are carried out prior to analysis using conventional methods, are not removed in the method of the present invention and therefore can be determined. Fifth, the method of the present invention requires no pretreatment of the sample, as is necessary before a sample is analyzed using presently-available methods. Pretreatment may result in a change in the composition of the sample and, concommitantly, a change in reactivity.

The method of the present invention is quick, simpler than presently available procedures and of value in human health care (e.g., in tests on blood samples), animal health care, the food processing industry and the pharmaceutical industry. It is particularly valuable in these contexts because it can be used in assays of whole blood and other samples (e.g., fermentation suspensions) which contain particulates, without first having to remove the particulates.

BRIEF DESCRIPTION OF THE DRAWINGS

As shown in FIG. 1, target site 1 can be a portion or region of a substance 2 which has additional components.

Specific binding site 5 is complementary to target site 1 and is a molecule or a portion of a molecule which can specifically interact with its complementary target site resulting in the formation of a ligating bond. As also shown in FIG. 1, specific binding site 5 can be a portion or region of a substance 6 which has additional components.

Figure 1:
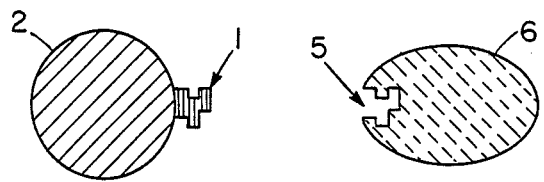
FIG. 1 is a schematic representation of a specific binding pair. One member of the pair has a target site 1 and the other has a specific binding site 5; target site 1 and specific binding site 5 in such a pair are complementary to each other. Target site 1 is a molecule or portion of a molecule which has a chemical configuration which can form a ligating bond with complementary binding site 5.
Figure 2:
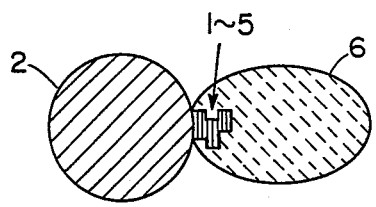

FIG. 2 shows ligating bond 1~5 formed between the two components of the specific binding pair of FIG. 1. Ligating bond 1~5 is formed between target site 1 and its complementary specific binding site 5.

Figure 3:
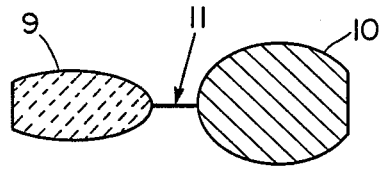

FIG. 3 is a schematic representation of the construct of the present invention, which is comprised of two moieties: (1) a moiety 9 which has either a specific binding site or a target site which forms a ligating bond with an appropriate site on particulates (indicator particles) present in a sample to be analyzed and (2) a moiety 10 which has either a specific binding site or a target site which forms a ligating bond with an appropriate site on an analyte of interest present in the sample. Moiety 9 and moiety 10 are joined into the construct of the present invention through link 11.

FIG. 4 depicts four configurations of the construct of the invention. FIG. 4a shows a construct of the present invention in which moiety 9a has a target site and moiety 10a has a noncomplementary specific binding site.

Figure 4A:
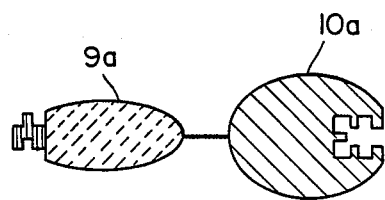
Figure 4B:
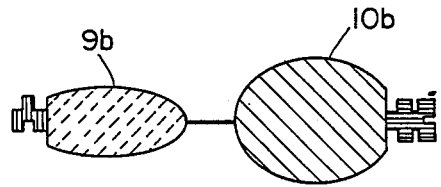

FIG. 4b shows a construct of the present invention in which each moiety has a target site; the target site of moiety 9b is different from the target site of moiety 10b.

Figure 4C:
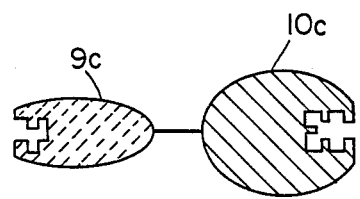

FIG. 4c shows a construct of the present invention in which each moiety has a specific binding site; the binding site of moiety 9c is different from the binding site of moiety 10c.

Figure 4D:
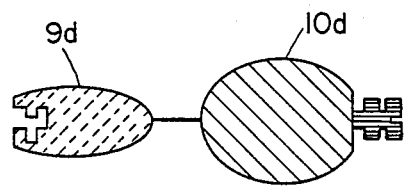

FIG. 4d shows a construct of the present invention in which moiety 9d has a specific binding site and moiety 10d has a non-complementary target site.

Figure 5:
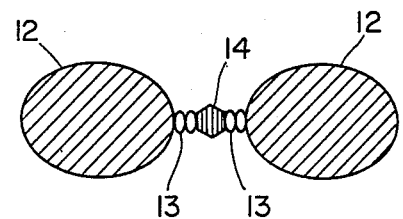

FIG. 5 is a schematic representation of the composition resulting from primary agglutination. Two indicator particles 12 are joined in the following manner: indicator particle 12 is joined to a construct 13 by a ligating bond (not shown) formed between indicator particle 12 and construct 13. Construct 13 is in turn joined to an analyte of interest 14 through a ligating bond (not shown). Analyte 14 is linked through a ligating bond (not shown) to a second construct 13, which is linked through a ligating bond (not shown) to a second indicator particle 12. In each case, the ligating bond is the same as that represented in FIG. 2 as 1~5. This results in a complex whose presence can be detected using known methods.

DETAILED DESCRIPTION OF THE INVENTION

The present invention relates to a method of carrying out ligand-binding assays, particularly immunoassays, and compositions (i.e., constructs and reagents) useful in such assays. It makes use of the fact that particulates present in a sample to be analyzed can be used as indicator particles in an assay to determine the presence and quantity of a bindable substance (analyte) in the sample. The method of the present invention can be carried out on particulate-containing samples, without pretreatment of the sample or processing to remove the particulates.

For purposes of defining and describing this invention, the following definitions are provided:

(1) Analyte (symbolized herein as "A"): a substance being detected in a particulate-containing sample.

(2) Binding site: that portion of a molecule, or multimolecule combination, which specifically interacts with a complementary chemical or physical configuration, referred to as a target site, such that, under appropriate conditions, the interaction results in formation of a ligating bond between the binding site and the target site. The bond is symbolized herein as "~". A binding site 5 is shown in FIG. 1.

(3) Target site: that portion of a molecule or multimolecule combination which has the chemical or physical properties or characteristics necessary for forming a ligating bond "~" with a binding site. A target site 1 is depicted in FIG. 1.

(4) Indicator particles: (symbolized herein as "P"): Any of a wide variety of particulates which are capable of being suspended in an aqueous environment. They are generally between 0.01 and 50 microns in diameter and comprise a heterogeneous mixture of chemical compounds encapsulated by a boundary membrane or film. Included in this definition are cells found in nature and subcellular structures such as nuclei, mitchondria, etc. Indicator particles have one or more binding site(s) and/or target site(s) available to form one or more ligating bond(s) with their target site(s) or binding site(s), respectively.

(5) Construct (symbolized herein as "p-a" and "a-p", which are equivalent and shown in FIGS. 3 and 4): A chemical compound designed and synthesized in such a manner as to chemically bind or otherwise join two moieties into one molecule: one moiety which binds to indicator particles and a second moiety which binds to an analyte of interest. In the construct represented in FIG. 3, moiety 9 binds to an indicator particle and moiety 10 binds to an analyte of interest. Each moiety has either a binding site or a target site and has specificity distinct from (i.e., different from) and not complementary to the other moiety present in the construct. Examples of constructs of the present invention are represented in FIG. 4.

Using the method and compositions of the present invention, it is possible to detect the presence of an analyte in a particulate-containing sample by incorporating into the sample a construct capable of binding or joining the analyte and the indicator particles. Particulates in the sample are used as indicator particles and are referred to in that manner. In a particulate-containing sample in which only one type of particulate occurs, the particulate serves as an indicator particle. However, in particulate-containing samples in which more than one type of particulate occurs, a specific type or specific types of particulate(s) is/are selected to serve as the indicator particle(s). For example, in whole blood, in which several types of particulates are present, red blood cells can be used as the indicator particle.

The construct used in the method of the present invention is designed and synthesized in such a way that two moieties are chemically bound or otherwise joined into one molecule, as shown in FIG. 3. One of the moieties in the construct binds to particulates in the sample; the other binds to the analyte of interest. Each of the moieties has a target site or a binding site and has specificity distinct from (i.e., different from) and not complementary to that of the other moiety.

In one embodiment of the present invention, referred to as the direct method of analysis, the construct is combined with a particulate-containing sample to be analyzed. This method is appropriate for detecting analytes which can bind at least two construct molecules. Binding of an analyte of interest to two construct molecules is represented in FIG. 5. If the analyte of interest is present in the sample, the result is agglutination or clumping of the indicator particles into a network comprised of the analyte, construct and indicator particles. As shown in FIG. 2, a ligating bond is formed as a result of the reaction between a specific binding site and a complementary target site. For example, chemical bonds, such as covalent bonds, hydrogen bonds, ionic bonds or salt bridges, hydrophobic interactions, etc., are formed between the specific binding site and the target site. FIG. 2 represents a ligating bond between 1 and 5, as a result of which 2 and 6 are joined. The presence and concentration of the analyte are determined by detecting the occurrence of agglutination of the particles and measuring the extent to which it occurs. The particulates thus serve as indicator particles.

In a second embodiment of the present invention, referred to as the indirect method of analysis, the construct as described above is used in combination with a second compound, referred to as a reagent. In this embodiment, the construct (which binds analyte or contains analyte and binds indicator particles), and the reagent, which is a polymeric form of the analyte entity or a polymeric form of the specific binding partner for the analyte, are combined with a sample to be analyzed. In the first case, in which a poly-analyte reagent is used, reagent can bind two or more construct molecules. In the second, in which poly-specific binding partner or agent is used, the reagent can bind two or more analyte molecules. This method is appropriate for detecting analytes, such as those which can bind to only one construct molecule, which cannot be detected by the direct method. The presence of analyte in the sample is demonstrated by lack of or reduction in agglutination of particulates. The lack of or reduction in agglutination occurs because the analyte of interest in the sample inhibits the formation of ligating bonds between construct and reagent.

Direct Method of Analysis

In one embodiment of the present invention, referred to as the direct method, the presence and quantity of an analyte of interest are determined in a particulate-containing sample by admixing with the sample (e.g., whole blood) a construct which is capable of binding with both the analyte of interest and particulates. Upon mixing of the construct with the sample, the following primary interactions occur among the primary (initial) reactants: analyte (A), particulates (P) and the construct (designated here p-a, which is the equivalent of a-p):

|  | Primary Reactants | Result of Interaction |
|---|---|---|
| (1) | P + A | No Reaction |
| (2) | p-a + p-a | No Reaction |
| (3) | P + p-a | P~p-a |
| (4) | A + a-p | p-a~A |

As is evident, some of the primary interactions result in binding of the primary reactants (reactions (3) and (4)). These are referred to as primary binding events.

In addition, secondary interactions subsequently occur (once P~p-A and p-a~A have been formed). The secondary binding reactions occur while reactions (3) and (4) above are continuing. The following interactions are possible:

|  | Primary Reactant | Primary Product | Secondary Result |
|---|---|---|---|
| (5) | P + | P~p-a | No Reaction |
| (6) | P + | p-a~A | P~p-a~A |
| (7) | A + | P~p-a | P~p-a~A |
| (8) | A + | p-a~A | No Reaction |
| (9) | p-a + | P~p-a | a-p~P~p-a |
| (10) | p-a + | p-a~A | p-a~A~a-p |

As is evident here, too, some of the secondary interactions result in binding of the interacting materials and others do not. Those resulting in binding are referred to as secondary binding events or reactions.

Note that the product of reactions (6) and (7) is the same compound: P~p-a~A.

Higher-order binding reactions occur between the primary reactants and the various products of reactions (3)–(10). See FIG. 5. As a result of these higher order reactions, many complex species are formed via different possible reaction paths.

For reactions (3)–(10) and higher order reactions to occur, the primary reactants have the following properties:

(i) analyte (A) is capable of binding with at least two construct molecules, as in reaction (10);

(ii) particulates (P) are capable of binding with one or more construct molecules, as in reactions (3) and (9);

(iii) construct p-a is capable of binding to at least one analyte A and to at least one particulate P, as shown as (5) and (8).

The construct (p-a) used for the direct method is capable of binding with sample particulates and with the analyte of interest. Binding to both the particulates and the analyte occurs as a result of ligating bonds being formed between complementary binding sites and target sites. A useful construct, therefore, can be designed to be appropriate for the nature of the particulates and the analyte in the sample being analyzed. For example, the following possibilities exist:

(i) The analyte may have at least two identical binding sites; these sites may occur as an integral part of the analyte, in the absence of or in addition to other binding properties. In this case, the construct is designed to have target sites of this repeated site as shown in FIG. 4a and FIG. 4b.

(ii) The analyte may have at least two identical target sites, which may be present in the absence of or in addition to other binding properties. In this case, the construct is designed to have complementary binding sites (FIG. 4c and 4d).

(iii) The analyte may have one or more of each of two or more binding sites; these may occur in the absence of or in addition to other binding properties. In this case, the construct comprises a mixture of different molecules, each of which has a target site to one of the binding sites.

(iv) This case is as in (iii), except that the target sites are associated with the analyte and binding sites are used to form the construct mixture.

(v) In this case, the analyte may have both one or more binding sites and one or more target sites. The appropriate construct is a mixture of the complementary target sites and binding sites.

Identical situations as those described above (i-v) exist for the properties of particulates and the design and synthesis of a useful construct. In all, great flexibility in the design of the construct is provided.

The following constraint exists in construct design and synthesis: constructs are produced which, in the absence of analyte, react only with particulates in the sample in such a manner that detectable agglutination of particulates does not occur.

Construct is prepared by joining together two moieties, one which can bind with particulates and one which can bind with an analyte of interest. The present invention is not limited by the nature of the linkage joining the two moieties but such linking must be of sufficient strength to maintain the integrity of the construct when the construct is serving to link indicator particles to analyte via ligating bonds.

In the present invention, the presence and quantity of the analyte can be determined by detecting the occurrence of construct binding to both particulates and analyte in such a manner as to join at least two indicator particles as in FIG. 5. Any method that detects this binding will be usable in practicing the invention. For example, particle counting methods, such as impedance particle counting, can be used to detect the ligation of two or more indicator particles in the presence of analyte.

Use of the Direct Method for Immunoassay of Antibodies

The direct method of detecting and quantifying an analyte according to the present invention can be used in the analysis of, for example, aqueous solutions containing particulates and antibodies (the analyte). It can be used to analyze cell cultures of antibody-producing cells and is particularly useful for detecting and quantifying antibodies in samples of whole blood. The use of the direct method of the present invention is illustrated below through a description of detection of antibodies in whole blood. It is to be understood that this is not be to limiting in any way.

The construct for such an assay consists of linked moieties designed to form ligating bonds with: (1) indicator particles selected from the particulates known to be present in a whole blood sample (preferably cellular entities such as red blood cells, white blood cells, platelets) and (2) the analyte of interest (i.e., the antibody to be determined). The analyte to be detected is, for example, an immunoglobulin (i.e., a protein), such as IgG, IgM, IgE, IgA, IgD, etc.

The component of the construct which is to bind with particulates (e.g., red blood cells) is referred to here as the particulate-binding moiety. It is selected from a group of substances which have either (1) binding sites, such as those present in antibodies, lectins, etc., to target sites naturally present on surfaces of cells such as antigens, membrane structural components, etc.; or (2) target sites complementary to binding sites naturally present on cell surfaces.

The moiety of the construct which is to bind with the analyte of interest (here, an antibody) is referred to here as the analyte-binding moiety. The analyte-binding moiety is preferably an antigen or antigens specific for the antibody to be determined. It is also possible to use other substances which form ligating bonds with the analyte antibody, such as haptens, antigen analogs, homologs or antagonists, anti-idiotypic antibodies, anti-immunoglobulin antibodies etc.

The two moieties of the construct selected to serve as the particulate-binding moiety and the analyte-binding moiety are joined by means of covalent linking or other chemical means, known to the art, which result in their linking. For example, bifunctional reactive compounds may be employed in linking the moieties. Such bifunctional compounds contain reactive groups that form covalent or other stable bonds with chemical groups present on the moieties. Reactive groups such as aldehyde, maleimide, imidizolide, lactone, lactam, active ester, azide, acyl active hydrogen, unsaturated acyl, etc., have been found to be useful in the bifunctional compounds. Additionally, compounds such as carbodiimides, that activate functional groups (e.g., carboxyls), present on the component substances may be selected to synthesize the construct.

A method useful in determining the presence and quantity of antibody in a sample (e.g., whole blood), preferably comprises the following steps:

(1) obtaining a sample of whole blood in a manner such that clotting of the blood does not occur (e.g., by collecting the sample in a heparin or other anticoagulant);

(2) mixing a volume of the blood sample with the construct. The construct will be either a solution (i.e., in water or other appropriate solvent) or a dry preparation;

(3) allowing the ligating reactions between the construct and the cellular components and between the construct and the analyte antibody, if present, to occur. This is accomplished by maintaining the combination formed in (2) under appropriate conditions (e.g., temperature, ionic strength, pH) for sufficient time for the reactions to occur;

(4) measuring or otherwise determining the extent of agglutination of blood cells by appropriate means, such as by visual detection, light scattering or absorption, particle counting or sizing, etc.;

(5) correlating the occurrence and degree of agglutination of the cells to the presence and quantity of analyte present. This can be done, for example, by reference to a pre-established standard curve.

It is an advantage of the present invention that known prior materials and techniques can be used to design and synthesize constructs and prepare reagents. Well-known techniques can also be used to carry out the analysis and read the results. These materials and techniques have been used, for example in immunoassay test reagents and immunoassays based on agglutination, enzyme immunoassay, radioimmunoassay, and fluorescent immunoassay. In presently-used immunoassay techniques for detecting antibodies in samples, the test reagent includes an antigen or antigens specific to the analyte antibody. These antigens may also be employed as the analyte-binding moiety of the construct of the present invention.

For example, a construct useful in the detection and quantification of antibody to rubella virus in human blood can comprise a particulate-binding moiety and a rubella-antibody-binding moiety joined together. The analyte-binding moiety useful in detecting antibody to rubella will be one or more antigens from rubella virus. Such antigens are well known and available; for example, they are presently used in commercial test kits for antibody to rubella which are available from Abbott Laboratories, Becton-Dickinson Company and Behring Diagnostics. Techniques used in preparing antigens from rubella virus for presently-used assays can be employed to prepare the analyte-binding moiety of the present invention.

In addition to the analyte-binding moiety, the construct of the present invention includes a particulate-binding moiety. In designing and synthesizing a construct useful for detecting antibodies in human blood, the particulate-binding moiety would preferably bind to red blood cells. The particulate-binding moiety can be selected from many substances (e.g., antibodies and lectins) that are known in the art. For example, rabbit antibody to sheep red cels are routinely employed for complement fixation tests, as described by Kabat in *Structural Concepts in Immunology and Immunochemistry*, pp 46–48 (1968). Lectins which form ligating bonds with red cells are commercially available from Sigma Chemical Co.; see, for example, 1986 Sigma Chemical catalog in which properties of lectins are presented and references are supplied.

When the method of the present invention is used to detect rubella antibodies in human blood, the particulate-binding moiety of the construct is selected from those substances capable of forming ligating bonds with human red blood cells; one particularly useful choice is one or more antibodies which bind human red blood cells. The particulate-binding moiety of the construct selected and used in a test for antibody to rubella may, of course, also be used in many other tests based on the present invention which use human red blood cells as indicator particles (e.g., hepatitis antibody antigens; bacterial antibodies, etc.).

The construct of the invention is synthesized by joining the particulate-binding moiety to the analyte-binding moiety. There are numerous compounds and methods useful in joining two molecules together (while retaining the activity of each moiety) which are well known in the art. For example, enzyme immunoassays are made possible by joining antibodies to enzymes while retaining the activity of each substance. Such techniques have been used for example, in preparing reagents included in kits available from Syva Company, Abbott Laboratories and Cordis Laboratories. As explained previously, any method of linking or joining two materials which results in a connection or linkage with sufficient strength to maintain the construct integrity while the construct is in use (i.e., serving to link indicator particles to analyte). The necessary compounds and methods ar well known in the art.

A construct useful in the rubella antibody test example is prepared by joining the particulate-binding moiety to the analyte-binding moiety. In this case, both moieties are proteins and, therefore, contain amino acid residues. Bifunctional linking compounds (e.g., commercially available with procedural documentation from Pierce Chemicals and others) react with the functional groups, such as hydroxyl, amino, thiol, and carboxyl groups of the proteins; this results in the two moieties being joined. The availability of asymmetric bifunctional linking compounds can be advantageously employed in the present invention to selectively join the two moieties into construct molecules. The construct molecules of the present invention will be of a molecular size and weight equal to the sum of the two moieties plus the linking compound; therefore, if necessary, they can be separated on the basis of their molecular size or weight from the unlinked moieties. This can be done, for example through the use of processes such as gel filtration chromatography (available from Pharmacia Fine Chemicals) electrophoresis and controlled pore size membrane filtration.

A reagent useful in detecting antibody to rubella can be prepared using the construct prepared to react with human red blood cells and with antibody to rubella virus antigens. The concentration of the construct in the reagent is selected so that: (1) in the absence of the analyte antibody (e.g., as is the case in known negative samples), no detectable agglutination of the red blood cells of the sample occurs and (2) in the presence of the analyte antibody, detectable agglutination occurs. An appropriate concentration of the construct to be used is selected and mixed in a solution of salts (e.g., NaCl, KCl, etc.) and pH buffers (e.g., phosphates, TRIS, HEPES, etc.) and other chemicals commonly used in commercially available test reagents. Such a mixture thus includes not only the construct, as the active ingredient, but also other ingredients which preserve the activity of the construct during storage and control the optimum reaction conditions of pH, ionic strength, etc., of the reaction mixture.

An example of a method of detecting antibodies to rubella virus antigens may include the following steps:
 (1) drawing human whole blood samples into an anticoagulant, such as heparin or EDTA, as is the current practice for cytology and hematology samples;

(2) mixing a small volume of blood (e.g., as little as 1 microliter but generally about 20 microliters or more) with a prescribed volume of the reagent (e.g., 100 microliters);

(3) maintaining the reaction mixture at room temperature sufficient time for agglutination to occur (e.g., several minutes); and (4) determining the presence or absence of antibody to rubella by visually detecting the presence or absence of agglutination of the red cells.

A reagent and method to detect antibodies to rubella in laboratories equipped with cell counters, such as those available from Coulter Electronics, differs from that described above in the concentration of the construct, which is selected to allow detection of the analyte antibody through measurement of aglutination on these instruments.

The present invention can be used for other antibodies in human blood samples as described above for rubella; in each case, one or more antigens specific for the analyte antibody of interest is included in the construct to be used. For example, an AIDS test can be prepared by employing HTLV-III antigens, either as obtained from HTLV-III virus or genetically engineered, (e.g., those presently used in tests available from Abbott Laboratories, Electronucleonics, Inc.) as the analyte-binding moiety and selecting the concentration of the construct to meet the requirements of AIDS testing.

It is a feature of the present invention that the blood of any species that contains red blood cells can be tested. The particulate-binding moiety of the construct is selected from substances that form ligating bonds with the cells of the species of interest. Tests for antibodies in animal blood, such as trichina antibodies in hog blood, can be provided.

In addition, particulate-containing samples, other than whole blood, can be used. By way of example, antibody can be detected in an in vitro culture of monoclonal antibody-secreting hybridoma cells. In these instances, the construct can be synthesized from a particulate-binding moiety that binds to, for example, mouse-mouse hybridoma cells, and an analyte-binding moiety specific for the antibody being produced.

The above descriptions are presented to illustrate the use of the present invention to detect antibodies. The constructs described can be modified as needed to detect other analytes of interest and the constructs and their uses described above are not intended to be limiting in any way.

Use of the Direct Method for Immunoassay for Antigens

The direct method can also be used to detect and quantify antigens in a sample, such as whole blood. The method used below is similar to that previously described for antibody detection and quantification.

This embodiment differs from the previously-described method for antibodies, however, in the analyte-binding substance that is one moiety of the construct. The construct used can be prepared from, for example, antibody or antibody fragments (e.g., Fab') which bind to cells present in the sample, and from antibody or antibody fragments which are reactive with the antigen to be determined. The antigen to be determined must be comprised of two or more target sites that react with the binding sites provided in the construct. The method of determination of the antigen will be the same as the assay for antibody described above.

For example, a test for hepatitis B surface antigen (HBsAg) in human blood can be carried out using a construct comprising (1) a particulate binding moiety, as described above with reference to rubella antibody and (2) an analyte-binding moiety selected from those substances, such as antibodies, known to bind to HBsAg. Antibodies to HBsAg which can be used are, for example, those presently used in commercially-available tests from Abbott Laboratories and Cordis Laboratories, and others. The antibodies can be of human or non-human origin. These two moieties, each containing functional groups of amino acid residues, are joined to form the construct, as described above in relation to the rubella antibody.

Similarly, tests for other antigens in human and non-human blood can be provided by employing specific antibodies or antibody fragments as the analyte-binding moiety of the construct. The reagent preparation and test methods are as described previously for antibody testing.

Use of the Direct Method for Non-Immunoassays for Substances

The direct method of the present invention, as described previously for use in determining antibodies or antigens can also be practiced for determining the presence of other substances (analytes) in a sample. The direct method is applicable to detection of analytes that have at least two binding sites or target sites, in samples which contain particulates that can bind with a construct.

For example, the method may be used to detect the presence and determine the quantity of receptors, binding proteins, carrier molecules, sequestering compounds, and other molecules or aggregates of molecules that form ligating bonds with hormones, activators, agonists, antagonists, inhibitors, substrates, cofactors, and molecules that contain two or more target sites. This can be done by using an appropriately-designed construct for the analyte to be determined; in this case the construct is designed to have binding activity complementary to that of the analyte.

The method of the present invention can also be practiced on samples other than human or animal blood samples. For example, it can be used to analyze samples which contain cells (e.g., samples obtained from microbial fermentation, tissue culture, etc.), by utilizing the cells that are present in the sample as the indicator particles.

By way of example, a construct useful in detecting active avidin in chicken blood will have a particulate-binding moiety that binds chicken red blood cells to which biotin, the analyte-binding moiety is joined. Any of the commercially available biotin derivatives, such as d-biotin-N-Hydroxysuccinimide ester available from Sigma Chemical Company, may be used to form the construct. Using this construct in the reagent, agglutination of the red blood cells will occur only when avidin, which has four biotin binding sites, is present in an active form capable of binding two or more biotin molecules present in the construct. An immunoassay for avidin, by contrast, would detect antigenically active avidin and, therefore, would not provide information on biotin binding activity in the blood.

Use of the Direct Method to Determine Particulate Associated Substances

The method and construct of the present invention can also be used to detect the presence and quantity of binding sites or target sites on the surfaces of cells, in a sample containing two or more types of particulates (e.g., whole blood). For example, the method may be useful for determining the presence and quantity of a specific type of cell (e.g., white cells, lymphocytes, basophiles, B-cells, infected cells, microbial cells, activated cells, immature cells, etc.) in the presence of another type of cell (e.g., red blood cells) in whole blood. The construct used is designed to form ligating bonds with both the analyte (which in this case is particulate) and the indicator cell type (which is a second, different particulate).

The ability to test for substances in whole blood using the present invention is particularly valuable in detecting cells or cell-associated analytes. For example, reagents are presently available from Ortho Diagnostics to perform T and B cell classification of human white blood cells. These tests require, in addition to the cell type specific antibodies, expensive instrumentation run by highly trained personnel. It is an object of the present invention to provide a construct comprising a moiety that will bind to human red cells joined to antibodies currently used to classify white cells. Due to the difference in relative concentration between red cells and white cells in human blood (5 million red cells compared to 4 to 10 thousand white cells per microliter), white cells of the type selected for by the analyte-binding moiety of the construct will be easily detectable, for example by microscopy, due to the presence of bound red cells.

In addition, the presence of bacterial cells in blood, either directly or after culture, can be detected by using analayte-binding moiety of the construct which binds to the bacteria of interest. For example, antibodies against the bacterial species may be employed. Alternatively, penicillin derivatives can serve as the analyte-binding moiety to detect the presence of bacteria that have penicillin-binding proteins as a component of their cell walls.

Indirect Method of Analysis

A second embodiment of the present invention, referred to as the indirect method, is useful in detecting analytes which cannot be detected by the direct method, as is the case when an analyte can bind to only one construct molecule. It is possible to detect such analytes by using two compositions: (1) a construct and (2) a reagent. In this method the particulate-binding moiety of the construct is the same as that described for the direct method.

In one application of the indirect method, the analyte-binding moiety is a component of the construct (as is the case, as described above, for the direct method) and the reagent is two or more analyte entities joined together and capable of binding two or more construct molecules.

In a second application of the indirect method, two or more analyte-binding moieties (e.g., an antibody specific for the analyte of interest), joined together, comprise the reagent. The construct in this case is the analyte, bound to the particulate-binding moiety. This application is illustrated in Example II.

Use of either of the two applications of the indirect method results in inhibition of agglutination of analyte is present. In either case, inhibition may be partial or complete, depending on the relative amounts of analyte and reagent present.

This embodiment of the present invention can be used to detect the presence and quantity of a substance which has a single, non-repeated target site or which can bind only one construct containing a target site. This is useful, for example, in analyzing samples for substances such as haptens, steroid hormones, low molecular weight drugs (typically having a molecular weight of less than 1,000), antibiotics, and binding proteins. If the method is used to detect and quantitate substances with monovalent binding properties, the following occurs: a construct which binds to the analyte and to the indicator particles in the sample is added to the sample; a polymeric form of the analyte entity is also added. If analyte is present in the sample, agglutination or clumping of the indicator particles is inhibited because the reagent competes with the analyte for binding to the construct. The result is reduction in the degree of clumping, which can be partial or complete inhibition of agglutination. Inhibition of agglutination is indicative of the presence of the analyte; the degree of inhibition is indicative of the quantity of the analyte in the sample.

The indirect method can rely on any of a variety of binding reactions, as described for the direct method. It can also be formatted to allow for, in addition to inhibition of clumping, reversal of clumping.

Examples of tests that can be performed using the indirect method include those known in the art of hapten assays. Included in this class are therapeutic drug monitoring tests, such as gentamicin, digoxin, phenobarbitol, phenytoin, and hormone tests, such as thyroxin, estrogen, cortisol. For example, a construct useful in a test for digoxin as the analyte in human blood would comprise a particulate-binding moiety (such as described above in relation to testing for rubella antibody) joined to the antibody to digoxin by methods previously discussed. Due to the nature of digoxin, in this instance, and haptens as a general class, the analyte can form a ligating bond with one and only one construct molecule.

It is an advantage of the present invention that by providing a reagent in addition to the construct, tests useful for detecting haptens can be performed. The reagent in the present example can comprise an oligomeric or a polymeric form of digoxin which can be prepared, for example, by: (1) specifically oxidizing the vicinal glycols present in digoxin to aldehydes using periodic acid; (2) mixing the oxidized digoxin with a suitable polymer containing a plurality of amino groups, such as human serum albumin or poly-lysine, to allow the formation of imine bonds between the aldehyde and amino groups; and (3) reducing the imines so formed to secondary amines linking digoxin to the polyamine with sodium cyanoborohydrate. These and similar reactions are commonly practiced in modifying haptens to impart antigenicity. These techniques can be employed in preparing oligomeric and polymeric forms of haptens other than digoxin.

Use of the indirect method of the present invention to test for haptens, such as digoxin, makes use of two reagents. A construct is prepared, as previously described, wherein the analyte-binding moiety specifically binds digoxin. In this case, however, agglutination of the red cells present in the sample occurs only in the presence of a reagent which is the polymerized analyte (here, digoxin). In this instance, the concentration of the construct and of the polymerized digoxin are selected such that when the sample is combined with the construct and the reagent, agglutination of the red cells occurs in the absence of analyte digoxin; in the presence of digoxin at clinically significant concentrations, detectable inhibition of agglutination occurs.

It is a particular advantage of the present invention that the breadth of applicability to a variety of analytes in a variety of samples described for the direct method embodiment is comparably broad using the indirect method due to the similar function performed by the construct in the two methods.

The present invention will now be illustrated by the following examples, which are not to be seen as limiting in any way.

EXAMPLE I

Whole Blood Immunoassay for Antibody

A. Preparation of Rabbit Polyclonal Antibodies that Agglutinate Human Red Blood Cells Human red blood cells (RBC's) were prepared from human blood by drawing blood into heparin anticoagulant and centrifuging the blood to remove the liquid plasma. After the white cells contained in the buffy coat were removed, the RBC pellet was resuspended in phosphate buffered saline (PBS) and the cells were washed and centrifuged. The washing step was repeated two times. The RBC's, free of plasma and white cell contaminants, were injected into rabbits following standard methods to cause rabbit antibodies to human RBC's to be elaborated. The antibody titer of the rabbits that had been injected was determined by collecting rabbit blood samples, clotting the samples and testing the antisera for human RBC agglutinating activity with whole human blood. Animals were selected on the basis of antibody titer and specificity for use in producing antibody to RBC's.

B. Preparation of Immunoglobulin Fragments

Immunoglobulin IgG was purified from rabbit antiserum by salting out, molecular sieving and ion exchange chromatography, using methods well known to those skilled in that art and reviewed by Kabat and Mayer in Experimental Immunochemistry (2nd ed. 1961) Chapter 49. F(ab')$_2$ fragments were prepared by pepsin digestion of the purified IgG. IgG fragments were separated from undigested IgG and contaminants by gel filtration chromatography. Fab' fragments were prepared using methods initially described by Nisonoff, A. and Mandy, W. H., Nature (London), 194: 355 (1962), from F(ab')$_2$ by reduction with 2-mercaptoethanol-amine at pH 5.5–6.0.

C. Preparation of Construct - TNP-Fab'

Fab' fragments prepared in B. above were allowed to react with 2,4,6-trinitrobenzene sulphonic acid. The resultant TNP-Fab' was purified from contaminants by dialysis. TNP-Fab' reagent was prepared by diluting the construct to approximately 2 micrograms per ml in PBS.

D. Whole Blood Immunoassay for Antibody

Human blood was collected into anticoagulant, such as with heparin. An aliquot of the blood was diluted with four parts of PBS. 50 microliters of the diluted blood was dispensed into microtiter plate wells. Into the first well, 100 microliters of a monoclonal antibody to TNP derived from in vitro culture of MOPC 315 cell line (American Type Culture Collection TIB 23) was added. This monoclonal antibody also reacts with DNP. Serial 1:2 dilutions of the antibody were performed, to a total of 24 wells. 50 microliters of the TNP-Fab' construct was added to each of the 24 wells and into 3 wells containing diluted blood and PBS without antibody to TNP. In addition, wells were set up that contained diluted blood and diluted antibody to TNP but no TNP-Fab'. The contents of the wells were mixed and allowed to settle for 15 minutes. Results were then read visually as described by Nichols and Nakamura to determine the patterns created by the settled red blood cells. The results were compared to patterns obtained in standard hemagglutination assays.

The results indicated that in the absence of antibody to TNP, absence of TNP-Fab' or at high dilutions of antibody to TNP (greater dilution than 1 to 4000), the cells settled in a pattern typical of negative hemagglutination tests. The pattern in negative hemagglutination tests was a "button pattern" with "trailing" when the plate was tilted and the settled cells were allowed to run down. In the wells containing low dilutions (less than 1 to 1024) of antibody to TNP, the cells settled into a pattern typical of positive hemagglutination tests; that is they formed a "lawn pattern" indicative of a complex network of cross linking of the cells due to binding reactions occurring between the cells derived from the whole blood sample, TNP-Fab' and antibody to TNP. In the wells containing intermediate dilutions of antibody to TNP, transitional patterns of settling were observed, indicating the occurrence of reactions typical of hemagglutination tests.

The readouts obtained were consistent with results expected by those skilled in hemagglutination testing. The method used, however, was considerably different from that used conventionally in that whole blood was used as the sample.

EXAMPLE II

Whole Blood Immunoassay for Haptens

A. Preparation of TNP-Fab' Construct

This reagent was prepared as in Example I.

B. Preparation of DNP-Lysine

This compound was purchased from Sigma Chemical, Inc.

C. Immunoassay for DNP-Lysine

Assay conditions that resulted in positive agglutination of sample RBC's by TNP-Fab' and antibody to TNP were selected from the assay in Example I. Using those conditions, an assay for TNP was set up by dispensing diluted blood into microtiter plate wells; adding the appropriate concentration of antibody to TNP to the wells; adding DNP-lysine to the first well and performing serial 1:2 dilutions for 23 additional wells. In the last step, the TNP-Fab' construct was added. Additional negative control wells were set up as in Example I. The contents of the wells were mixed and the reaction was allowed to proceed for 15 minutes. As in Example I, the results were read visually and compared to hemagglutination test patterns.

The results of this assay demonstrated that in the presence of sufficiently high concentrations, at least 10 micrograms per milliliter, of DNP-lysine, red cell agglutination was prevented by competitive inhibition of agglutination by DNP-lysine. Agglutination inhibition followed a dose response curve and did not occur at high dilutions of DNP-lysine, that is at concentrations of 1 microgram per ml and below. DNP-lysine was used in the work described in this Example because it is a well-acknowledged model of a hapten.

EXAMPLE III

Verification of Construct Binding to Cells

Experiments were conducted to demonstrate that in the absence of agglutination, reaction occurred between the cells and Fab' portion of the construct. Antibody that reacted with rabbit Fab' was purchased commercially from Sigma Chemical Co.; its reactivity was confirmed by immunoprecipitation reaction. Other materials required were prepared as described in Example I.

Diluted human blood was dispensed into microtiter plate wells in two duplicate plates. Fab' or TNP-Fab' were added to multiple wells in the plates. Antibody to TNP was added to wells containing either Fab' or TNP-Fab' at two concentrations selected on the basis of results obtained in Example I: a high concentration, obtained by diluting MOPC 315 antibody to TNP 1 to 500, and a low concentration, obtained by diluting the antibody to TNP to a 1 to 5000 dilution. Antibody to Fab' was added to the wells in one plate and an equal volume of PBS without antibody to Fab' was added to the other plate. The reaction was allowed to proceed and the results were read as described in Example I.

The following results were obtained: In the absence of antibody to TNP, at either dilution, and in the absence of antibody to Fab', no agglutination occurred; in the presence of TNP-Fab' and antibody to TNP at high concentration, the expected agglutination resulted. In the presence of Fab' or TNP-Fab' and in the presence of antibody to Fab', agglutination resulted. These results, combined with the finding that antibody to Fab' did not cause agglutination in the absence of Fab', indicate that Fab' and TNP-Fab' react with the cells even in the absence of agglutination and that agglutination relates specifically to the presence or absence of the analyte being determined.

EXAMPLE IV

Assays with Undiluted Blood

The assays described in Example I and II were performed using the materials prepared therein. The assays were, however, carried out with a concentration and quantity of the construct used in Examples I and II selected so that dilution of the blood prior to analysis was not necessary. The results obtained using this assay format were entirely consistent with the results described in Examples I and II, which used diluted whole blood.

EXAMPLE V

Assays Using Monoclonal Antibodies

Preparation of Mouse Monoclonal RBC-Agglutinating Antibodies

RBC inoculates, prepared from either pig or cow blood as in Example I.A., were injected into Balb-C mice following standard procedures. The antibody titer of each mouse was determined in microtiter plate agglutination assays against whole blood. Spleen cells were prepared for fusion with NS-1 myeloma cells; hybridomas were formed and dispensed into tissue culture wells. The wells that contained viable cells which secreted antibody which agglutinated RBCs were determined by testing supernatant media against whole blood. Cell colonies producing usable antibodies were subcloned and maintained to produce monoclonal antibodies to RBCs by in vivo and in vitro culture methods.

The monoclonal antibodies thus produced were used to prepare the red blood cell-binding moiety of the construct. This construct performed in agglutination assays as did the fragments prepared from rabbit polyclonal antibodies.

Preparation of Monoclonal Mouse Immunoglobulin M and Assay Using Human Whole Blood Monoclonal mouse immunoglobulin M (IgM), which reacts with human red blood cells, was prepared. Antibody was produced by growing hybridoma cells as ascites or in culture and is referred to as FE1. Ascites fluid was diluted with Tris-sodium chloride (saline) buffer (pH 7.4) and titrated against human red blood cells (type O) diluted 1:3 in a microtiter plate. FE1 was diluted serially. Results were obtained visually. FE1 at a dilution of less than 1:40,000 resulted in agglutination. No agglutination occurred at higher dilutions.

400 microliters of a 1:10 of antibody and 100 microliters of mercaptoethanolamine were combined, under reducing conditions, in the Tris-saline buffer (pH 7.4) for 10 hours at room temperature. Titration of the reduced FE1 (FE1R) indicated agglutination occurred at a titer of less than 1:5000.

A dilution of 1:25 FE1R in Tris-saline buffer (pH 7.4) and bovine serum albumen (BSA) was made. This was used as the reduced antibody stock solution.

Anti-mouse IgM was mixed with human whole blood (type O). Reduced antibody (FE1R), in the stock solution described above, was added to the mixture at various concentrations. Agglutination of cells occurred at a 1:10,000 dilution of FE1R, indicating FE1R is binding to the red blood cells. The formation of Anti-IgM - FE1R subunits-human red blood cells complexes results in the agglutination observed (by the unaided eye). In control mixtures with no anti-IgM, FE1R alone caused no observable agglutination.

Equivalents

Those skilled in the art will recognize, or be able to ascertain using no more than routine experimentation, many equivalents to the specific embodiments of the invention described herein. Such equivalents are intended to be encompassed by the following claims.

I claim:

1. A method of determining a analyte of interest in a particulate-containing sample, comprising the steps of:
   a. contacting the sample with a construct comprised of a first moiety which binds to particulate present in the sample as obtained, but not to the analyte of interest and a second moiety which binds to the analyte of interest, under conditions appropriate for binding of particulate to the first moiety of the construct and binding of analyte to the second moiety of the construct, thereby resulting in formation of complexes comprised of analyte, construct and particulate; and
   b. detecting the presence of complexes comprised of analyte, construct and particulate.

2. The method of claim 1 wherein the particulate-containing sample is whole blood.

3. The method of claim 2 wherein the quantity of analyte present in the sample is determined by determining the extent to which complexes are formed.

4. The method of claim 2 in which:
a. the analyte of interest is an antibody; and
b. the construct is comprised of:
1. a first moiety selected from the group consisting of substances containing target sites to binding sites present on surfaces of particulates in the sample and substances containing binding sites complementary to target sites present on surfaces of particulates in the sample and
2. a second moiety selected from the group consisting of antigens specific for the antibody which is the analyte of interest and other substances which form ligating bonds with the antibody which is the analyte of interest.

5. A method of determining an antibody of interest in whole blood, comprising the steps of:
a. contacting a sample of whole blood with a construct comprised of a first moiety which binds to red blood cells but not to antibody of interest and a second moiety which is an antigen or a substance which forms ligating bonds with the antibody of interest, under conditions appropriate for binding of red blood cells to the first moiety of the construct and for binding of antibody to the second moiety of the construct, binding resulting in agglutination of red blood cells present in the sample; and
b. detecting agglutination of red blood cells.

6. The method of claim 5 wherein antibody of interest present in the sample of whole blood is quantitated by determining the extent to which agglutination of red blood cells occurs.

7. A method of determining an antigen of interest in whole blood, comprising the steps of:
a. contacting a sample of whole blood with a construct comprised of a first moiety which binds to red blood cells but not to antigen of interest and a second moiety which is an antibody specific for the antigen of interest, under conditions appropriate for binding of red blood cells to the first moiety and for binding of the antigen of interest to the second moiety, binding resulting in agglutination of red blood cells present in the sample; and
b. detecting agglutination in the sample.

8. The method of claim 7 wherein the antigen of interest present in the sample of whole blood is quantitated by determining the extent to which agglutination of red blood cells occurs in the sample.

9. A method of determining in whole blood an analyte of interest having at least two binding sites or at least two target sites, comprising the steps of:
a. obtaining a sample of whole blood in such a manner that clotting does not occur;
b. contacting the sample with a construct comprised of a particulate-binding moiety which binds to red blood cells present in the sample as obtained, but not to analyte of interest and an analyte-binding moiety which binds to the analyte of interest, under conditions appropriate for binding of particulates to the particulate-binding moiety and for binding of analyte to the analyte-binding moiety, binding resulting in agglutination of red blood cells; and
c. detecting agglutination in the sample.

10. The method of claim 9 wherein the analyte of interest is quantitated by determining the extent to which agglutination occurs.

11. The method of claim 9 in which the analyte of interest is an antigen and the analyte-binding moiety of the construct is an antibody specific for the antigen.

12. The method of claim 9 in which the analyte of interest is an antibody and the analyte-binding moiety of the construct is an antigen which binds specifically with the antibody of interest.

13. The method of claim 9 in which the analyte of interest is a receptor.

14. The method of claim 9 in which the analyte of interest is an enzyme.

15. The method of claim 9 in which the analyte of interest is a binding protein.

16. The method of claim 9 in which the analyte of interest is a carrier molecule.

17. The method of claim 9 in which the analyte of interest is a sequestering compound or a molecule which forms a ligating bond with a hormone.

18. The method of claim 9 in which the analyte of interest is an activator.

19. The method of claim 9 in which the analyte of interest is an agonist.

20. The method of claim 9 in which the analtye of interest is an antagonist.

21. The method of claim 9 in which the analyte of interest is an inhibitor.

22. The method of claim 9 in which the analyte of interest is a substrate.

23. The method of claim 9 in which the analyte of interest is an cofactor.

24. The method of claim 9 in which the analyte of interest is a molecule having at least two binding sites.

25. The method of claim 9 in which the analyte of interest is bound to a cell.

26. The method of claim 25 in which the analyte of interest is an antigen.

27. The method of claim 25 in which the analyte of interest is an antibody.

28. The method of claim 25 in which the analyte of interest is a receptor.

29. The method of claim 25 in which the analyte of interest is an agonist.

30. The method of claim 25 in which the analyte of interest is an antagonist.

31. A method of quantitating an analyte of interest in a particulate-containing sample, the analyte of interest having one binding site or one target site, comprising the steps of:
a. contacting the particulate-containing sample with a construct and a reagent, the construct comprising a particulate-binding moiety which binds to particulates present in the sample as obtained, but not to analyte of interest and an analyte-binding moiety which binds to analyte of interest and the reagent comprising at least two analyte entities, the analyte and the reagent competitively binding with the construct, under conditions appropriate for binding of particulates to the particulate-binding moiety and for binding of analyte to analyte-binding moiety; and
b. determining the extent of inhibition of agglutination in the sample.

32. The method of claim 31 wherein the particulate-containing sample is whole blood.

33. The method of claim 32 in which the analyte of interest is a hapten.

34. The method of claim 32 in which the analyte of interest is a steroid hormone.

35. The method of claim 32 in which the analyte of interest is a low molecular weight drug.

36. The method of claim 32 in which the analyte of interest is an antibiotic.

37. The method of claim 32 in which the analyte of interest is a binding protein.

38. A method of quantitating an analyte of interest in a particulate-containing sample, the analyte of interest having one binding site or one target site, comprising the steps of:
a. contacting the particulate-containing sample with a construct and a reagent, the construct comprising a first moiety which binds to particulates present in the sample as obtained, but not to analyte of interest and a second moiety which is the analyte of interest and the reagent comprising at least two analyte-binding moieties which bind the analyte of interest, under conditions appropriate for binding of particulates to the particulate-binding moiety and for binding of analyte of interest to analyte-binding moieties; and
b. determining the extent of inhibition of agglutination in the sample.

39. A composition for detecting an analyte of interest in a particulate-containing sample, comprising a construct consisting essentially of two moieties joined together: a first moiety which binds to selected particulates present in the sample as obtained, but not to the analyte of interest and a second moiety which binds to the analyte of interest.

40. The composition of claim 39 wherein the analyte of interest is an antibody and the second moiety is selected from the group consisting of antigens specific for the antibody which is the analyte of interest and other substances which form ligating bonds with the antibody which is the analyte of interest.

41. The composition of claim 39 for detecting an antibody of interest in a sample of whole blood.

42. The composition of claim 39 additionally comprising a reagent which has at least two identical components which are the analyte of interest and which binds to the construct competitively with the analyte.

43. A composition of claim 39 additionally comprising a reagent comprising at least two analyte binding moieties which bind the analyte of interest.

44. A composition for detecting an analyte of interest in a particulate-containing sample, comprising a construct consisting essentially of two moieties joined together: a first moiety which binds to selected particulates present in the sample as obtained, but not to the analyte of interest and a second moiety which is the analyte of interest.

45. A construct for detecting an analyte of interest in a whole blood sample, consisting essentially of two moieties joined together: a first moiety which binds to red blood cells but not to the analyte of interest and a second moiety which binds to the analyte of interest.

46. The construct of claim 45 wherein the analyte of interest is an antibody and the second moiety is selected from the group consisting of antigens specific for the antibody which is the analyte of interest and other substances which form ligating bonds with the antibody which is the analyte of interest.

47. A construct for detecting an analyte of interest in a sample of whole blood, the analyte having at least two binding sites or at least two target sites, consisting essentially or two moieties joined together: a first moiety which binds to selected cells present in whole blood as obtained, but not to the analyte of interest and a second moiety which binds to the analyte of interest.

48. The construct of claim 47 wherein the first moiety is an antibody which binds a surface antigen of red blood cells present in the sample, or a fragment of said antibody.

49. A composition for detecting an analyte of interest in a sample of whole blood, the analyte having one binding site or one target site, comprising (a) a construct consisting essentially of two moieties joined together: a first moiety which binds to selected cells present in whole blood as obtained, but not to the analyte of interest and a second moiety which binds to the analyte of interest, and (b) a reagent comprised of at least two analytes, binding of the analyte of interest with the second moiety and of the reagent with the second moiety being competitive.

50. A kit useful for determining an analyte of interest in a particulate-containing sample, comprising a collection of reagents for forming agglutination complexes, said collection of reagents including a construct consisting essentially of two moieties joined together: a first moiety which binds to selected particulates present in the sample as obtained, but not to the analyte of interest and a second moiety which binds to the analyte of interest.

51. A construct for detecting an analyte of interest in a whole blood sample, consisting essentially of two moieties joined together: a first moiety which binds to red blood cells but not to the analyte of interest and a second moiety which binds to the analyte of interest, in which the first moiety or the second moiety, but not both moieties, can be an immunoglobulin.

52. A construct for detecting an analyte of interest in a sample of whole blood, the analyte having at least two binding sites or at least two target sites, consisting essentially of two moieties joined together: a first moiety which binds to selected cells present in whole blood as obtained, but not to the analyte of interest and a second moiety which binds to the analyte of interest, in which the first moiety or the second moiety, but not both moieties, can be an immunoglobulin, the two moieties joined by other than a thiol bond derived from at least one part of the interchain disulfide bond of an immunoglobulin.

* * * * *